United States Patent
Herrnsdorf

(10) Patent No.: US 9,015,884 B2
(45) Date of Patent: Apr. 28, 2015

(54) HEAD SUPPORT FOR STOPPING SNORING

(71) Applicant: Johannes Herrnsdorf, Herdecke (DE)

(72) Inventor: Johannes Herrnsdorf, Herdecke (DE)

(73) Assignee: Nitetronic Holding Limited, Grand Cayman (KY)

( * ) Notice: Subject to any disclaimer, the term of this patent is extended or adjusted under 35 U.S.C. 154(b) by 0 days.

(21) Appl. No.: 14/358,625

(22) PCT Filed: Nov. 16, 2012

(86) PCT No.: PCT/EP2012/072923
§ 371 (c)(1),
(2) Date: May 15, 2014

(87) PCT Pub. No.: WO2013/072505
PCT Pub. Date: May 23, 2013

(65) Prior Publication Data
US 2014/0310878 A1 Oct. 23, 2014

Related U.S. Application Data

(60) Provisional application No. 61/636,160, filed on Apr. 20, 2012, provisional application No. 61/636,168, filed on Apr. 20, 2012.

(30) Foreign Application Priority Data

Nov. 16, 2011 (DE) .......................... 10 2011 118 614
Mar. 27, 2012 (DE) .......................... 10 2012 006 024

(51) Int. Cl.
*A47G 9/10* (2006.01)
*A61F 5/56* (2006.01)

(52) U.S. Cl.
CPC .... *A47G 9/10* (2013.01); *A61F 5/56* (2013.01)

(58) Field of Classification Search
USPC .............................. 5/639–641, 644–645, 636
See application file for complete search history.

(56) References Cited

U.S. PATENT DOCUMENTS

| | | | | |
|---|---|---|---|---|
| 5,421,044 A | * | 6/1995 | Steensen | 5/710 |
| 6,386,201 B1 | * | 5/2002 | Fard | 128/848 |
| 7,100,227 B2 | * | 9/2006 | Frisbee | 5/640 |
| 8,176,921 B2 | | 5/2012 | Bazargani | |

(Continued)

FOREIGN PATENT DOCUMENTS

| | | |
|---|---|---|
| DE | 9100663 U1 | 4/1991 |
| DE | 199 30 818 C1 | 5/2001 |

(Continued)

OTHER PUBLICATIONS

Form PCT/ISA/210 issued in PCT/EP2012/072923 dated Feb. 5, 2013 with English translation (6 pages).

(Continued)

*Primary Examiner* — Fredrick Conley
(74) *Attorney, Agent, or Firm* — Flynn, Thiel, Boutell & Tanis, P.C.

(57) ABSTRACT

A head support for stopping snoring of a sleeping individual, wherein the head support has a head resting surface for the head of a sleeping individual to rest on, including an active layer with an arrangement of neighboring deforming elements for controlling the height of the head support section by section, and a sensing layer which is arranged between the head resting surface and the active layer to detect a position of the head resting on the head resting surface.

19 Claims, 2 Drawing Sheets

(56) References Cited

U.S. PATENT DOCUMENTS

| | | |
|---|---|---|
| 2003/0221261 A1 | 12/2003 | Torbet et al. |
| 2004/0177449 A1 | 9/2004 | Wong et al. |
| 2007/0061976 A1 | 3/2007 | Bazargani |
| 2007/0240723 A1 | 10/2007 | Hong et al. |
| 2009/0094750 A1 | 4/2009 | Oguma et al. |

FOREIGN PATENT DOCUMENTS

| | | |
|---|---|---|
| DE | 101 28 095 A1 | 4/2003 |
| DE | 201 21 693 U1 | 4/2003 |
| DE | 10 2004 022 284 B3 | 12/2005 |
| DE | 10 2004 034 816 A1 | 2/2006 |
| DE | 10 2011 118 614 B3 | 2/2013 |
| WO | WO 2005/013868 A1 | 2/2005 |

OTHER PUBLICATIONS

Form PCT/IB/373 International Preliminary Report on Patentability issued in International Application No. PCT/EP2012/072923 dated May 20, 2014 (1 page).

Form PCT/ISA/237 English translation of Written Opinion of the International Searching Authority issued in International Application No. PCT/EP2012/072923 date of mailing Feb. 5, 2013 (6 pages).

* cited by examiner

HEAD SUPPORT FOR STOPPING SNORING

CROSS REFERENCE TO RELATED APPLICATIONS

This application is the National Stage of International Application No. PCT/EP2012/072923, filed Nov. 16, 2012, which claims the benefit of U.S. Provisional Application Ser. Nos. 61/636,160 and 61/636,168, both filed Apr. 20, 2012.

TECHNICAL FIELD

The present invention relates to head supports, in particular pillows. Furthermore, the present invention relates to measures for reducing snoring of an individual who rests on a head support.

PRIOR ART

A high percentage of individuals snore while sleeping. Snoring reduces the oxygen intake of the body and is nowadays known for provoking various diseases. A sleeping individual, however, does not perceive its own snoring so that it cannot readily be stopped by the individual on its own.

From prior art, various approaches are known to stop snoring of a sleeping individual. Devices that move the sleeping individual when any snoring occurs or which stimulate the individual to change its position on its own are preferred in contrast to means that are directly attached onto the body or are directly inserted into the body, as they are more easily tolerated by the individuals concerned.

From document DE 20 121 693 U1, a device for preventing snoring is known having an actuating unit for a head support of a sleeping individual which can be controlled by a control unit wherein, when snoring occurs, the head support is activated to transfer vibrations onto the head of the sleeping individual so that the sleeping individual stops snoring.

From document DE 101 28 095 C2, a pillow for preventing the occurrence of snoring is known wherein at least one pressure chamber filled with a medium produces continuous steplessly controllable intervallic movements of the pillow by changing its volume wherein no harmful electrical fields are generated in the pillow.

To stop the snoring of an individual who rests on a head support by means of a change of a head position, it is necessary to detect the position of the head on the head support with an acceptable accuracy so that the head can be moved selectively.

From document DE 199 30 818 C1, a device for preventing snoring is known which has a pillow, a sound sensor for detecting snoring noises and a control unit which can be activated by the snoring noises. The control unit controls a position change of the head of the sleeping individual by moving the pillow. For that purpose there is provided an airbag divided into chambers in the pillow wherein the air pressure of the chambers can be controlled by the control unit in conjunction with at least one air pressure source and an air pressure reduction unit. The position of the head of the sleeping individual can be determined from the increase of the pressure in the chambers on which the head is rested, resulting from the weight of the head.

The provision of pressure sensors to detect the air pressure in the chambers of the air bag is technically expensive and it is therefore desirable to provide a simplified detection of the position of the head of the head support.

From document DE 10 2004 034816 B4, a device for supporting the head of a lying person is provided with a plurality of lifting units. A flexible layer is arranged at a lower edge of the device which is directed to the body of the individual in which a plurality of pressure and temperature sensors, respectively, are located along the whole width of the layer to detect the body position. Such a device, however, is capable of detecting the body position of the individual resting on the head support, but not the head position resting on the head support.

It is an object of the present invention to provide a head support which allows detection of the position of the head of an individual resting on the head support in an improved manner. A further object of the present invention is to provide improved comfort for an individual resting on the head support.

SUMMARY OF THE INVENTION

According to a first aspect, a head support is provided for stopping snoring of a sleeping individual, wherein the head support has a head resting surface for the head of a sleeping individual to rest on. The head support includes:
  an active layer with an arrangement of neighboring deforming elements for controlling the height of the head support section by section;
  a sensing layer which is arranged between the head resting surface and the active layer to detect a position of the head lying on the head resting surface.

One idea of the above head support is to provide a sensing layer between a head resting surface of the head support and an active layer which includes deforming elements to detect the position of the head of an individual resting on the head support, wherein the sensing layer has several separate sensing layers so that a position of the head of an individual resting on the head support can be determined on the head resting surface. Such an arrangement can be simply made, and, in particular, sensors to measure the pressure in the deforming elements provided as chambers can be omitted.

Furthermore, a stiffening element can be provided to counteract a deflection of the active layer in the direction of a weight force of the head resting on the head resting surface.

To have an improved position detection of the head at a given accuracy of the sensing layer, there is provided the stiffening element for stiffening the active layer so that the arrangement of the deforming elements is maintained when a head rests on the head support. Particularly, the stiffening element shall have the effect that, at the position at which the head rests on the head support, the deforming elements do not bulge on the opposing side of the active layer, since thereby the sensing layer would also be deformed which might result in inaccurate and unreliable detection of the position of the head, respectively. In fact, the detection of the position of the head could be improved by an increased resolution of the sensing layer; this is, however, costly, and it can be achieved by the stiffening element for stiffening the active layer, in that a sensing layer with relatively low resolution can be used to maintain the accuracy of the detection of the position of the head on the head support.

According to an embodiment, the stiffening element can include a backing layer which is arranged on the side of the active layer opposing the sensing layer to support/back the active layer.

It may be provided that the active layer is attached to the backing layer particularly by means of an adhesive or by sewing wherein additionally or alternatively the active layer is attached to the sensing layer particularly by an adhesive or by sewing.

According to an embodiment, the backing layer can be sandwiched between a base layer and the active layer, wherein the base layer has a lower stiffness than the backing layer.

Furthermore, a comfort layer can be sandwiched between the head resting surface and the sensing layer wherein the base layer and the comfort layer together fully enclose the backing layer, the active layer and the sensing layer.

Particularly, the active layer can comprise a number of first deforming elements which are neighboring along a cross-direction in a row, and one or more second deforming elements which are offset with respect to a longitudinal direction perpendicular to the cross-direction along the row or first deforming elements which are neighboring along the cross-direction.

The deforming elements of the active layer can include chambers filled with a medium wherein the medium is supplied via a conduct by means of a pump provided external of the head support wherein a sound-dampening device may be arranged on or in the conduct to dampen vibrations in the medium.

Furthermore, the sensing layer can include sensing sections with one or more resistive, capacitive pressure sensors, one or more pressure-sensitive contact elements or one or more temperature sensors wherein the sensing sections are arranged so that the position of the head can be detected by identifying one or more of the sensing sections on which the head rests/lies on.

According to an embodiment, it can be provided that the sensing layer has a position sensor which is configured to determine an indication about a position of the head resting on the head resting surface by means of a capacitive, inductive or resistive measurement technique.

According to a further aspect, a system is provided including:

the above head support, a control unit to actuate the deforming elements of the active layer depending on a position of the head on the head resting surface detected by means of the sensing layer to change the position and/or the orientation of the head.

Furthermore, the control unit can be configured to detect the snoring of an individual resting on the head support and to actuate the deforming elements to change the position and/or the orientation of the head when the snoring has been detected.

BRIEF DESCRIPTION OF THE DRAWINGS

Preferred embodiments of the present invention are described in more detail in conjunction with the accompanying drawings in which.

DESCRIPTION OF EMBODIMENTS

Figure 1:
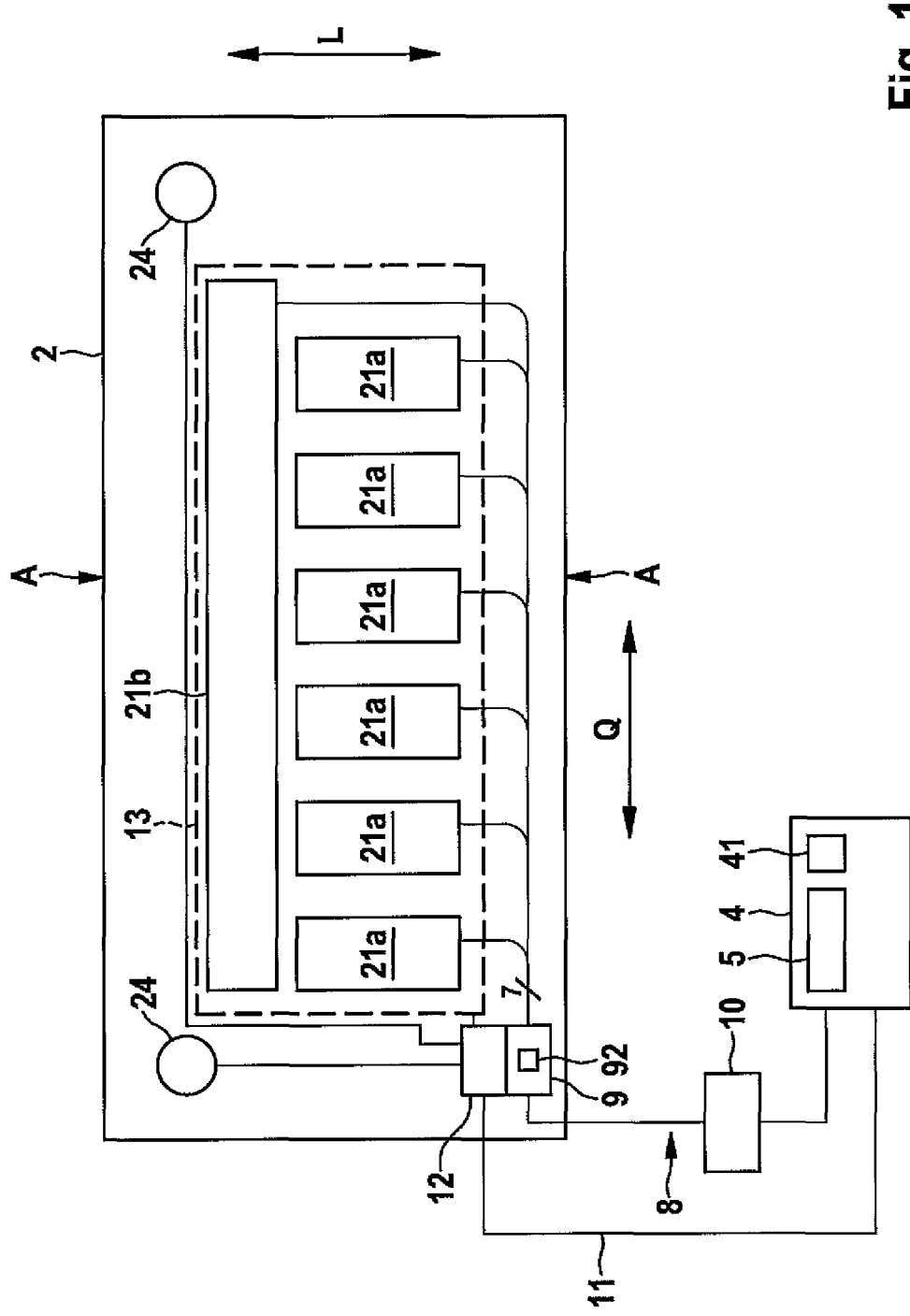
FIG. 1 shows a representation of the overall system to operate a head support for stopping snoring.

FIG. 1 shows a schematic representation of a system 1 for stopping snoring. The system 1 includes a head support 2 which may serve as active pillow for a sleeping individual or as active underlay for the head of a sleeping individual. Furthermore, the head support 2 is connected with a control unit 4 which controls the functions of the head support 2. In an alternative embodiment, the control unit 4 can be integrated in the head support.

The head support 2 has a substantially rectangular shape with a cross-direction Q and a longitudinal direction L. The head support 2 shall be arranged in a bed so that the cross-direction Q corresponds to the width direction of the bed or the lying surface, respectively, and the longitudinal direction L corresponds to the longitudinal direction of the bed or the lying surface, respectively. As further shown in conjunction with the side view of the head support 2 of FIG. 2, the cross-section of the head support 2 with respect to the cross-direction Q is provided with a varying height in the height direction. Particularly, the head support 2 includes a recess 22 to define the position of the head of a sleeping individual with respect to the longitudinal direction L. This is advantageous, as a desired tilting movement of the head in the longitudinal direction L is facilitated thereby.

Figure 2:
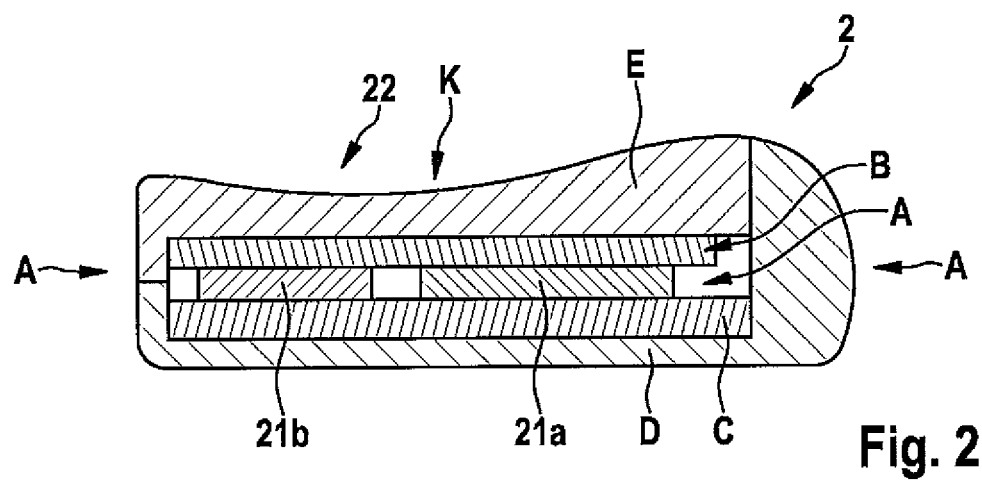
FIG. 2 shows a cross-sectional view of the layer arrangement of the head support.

As shown in FIG. 2, the head support 2 includes an active layer A which includes a number of neighboring (i.e. in the cross-direction and/or in the longitudinal direction) deforming elements 21. The deforming elements 21 can be actuated appropriately to deform, particularly to increase or decrease the height of the head support 2 at their respective position (with respect to a direction both perpendicular to the cross-direction Q and perpendicular to the longitudinal direction L).

The deforming elements 21 can be configured for the shown embodiment as chambers made of flexible material which can be gas-filled, particularly as air chambers. The chambers can be filled with a fluid, e.g. a gas, for instance air, or with liquid, for instance a gel or water. The amount of fluid that is put into the chambers determines the deformation of the deforming elements 21 in the head support 2, particularly their thickness so that the height of the head support 2 at the position of the corresponding deforming element 21 can be varied selectively.

A reservoir containing fluid to be supplied to the chambers can be provided in the interior of the head support 2 or separately therefrom. In the present embodiment, the control unit 4 is provided external the head support 2 and includes a pump for the medium by means of which the chambers are to be filled, particularly an air pump 5. The pump or the air pump 5, respectively, can be configured as a diaphragm pump and can be alternatively arranged external to the control unit 4.

The air pump 5 intakes environmental air and supplies it under an increased pressure. Alternatively, a pressured air tank can be provided instead, or additionally to the air pump 5, wherein the pressured air tank can be filled or replaced at non-sleeping times to avoid pumping noise of the air pump 5 during the sleeping times.

The air pump 5 is connected with the head support 2 via an air conduct 8. As the operational noise of the pump 5 can be transmitted via the air conduct 8 into the head support 2, a noise-damping device 10 can be arranged in the air conduct 8 connected with the head support 2, wherein the noise-damping device 10 is configured to dampen or to suppress a sound transmission through the air in the air conduct 8 towards the head support 2. The noise-damping device 10 can be provided with a volume through which the air to be transferred into the chamber can be guided. The volume can be a void/hollow volume or can include a noise-dampening material.

Instead of chambers filled with a medium, the deforming elements of the active layer A can be configured as electromechanical actuators or the like, as long as these can effect a selective height change of the section of the head support 2.

The number and arrangement of the deforming elements 21 of the active layer is selected so that a tilting or turning of a head resting on the head support 2 with respect to at least one direction, preferably a cross-direction Q, can be performed. For this purpose, a row of similar first deforming elements 21*a* is arranged neighboring along a cross-direction Q. The first deforming elements 21*a* can have a rectangular cross-section with respect to the height direction of the head support 2 with a shorter side in cross-direction Q. Also, a polygonal, circular, oval or alveolar configuration of the first deforming elements 21*a* can be provided.

By selective deforming/actuating of the first deforming elements 21*a*, a turning or tilting movement of the head resting thereon into the cross-direction Q can occur. This can be achieved particularly by differently deforming two neighboring first deforming elements 21*a* above which the resting area of the laid-on head extends. In case of fillable chambers as deforming elements 21, this can be achieved in that one chamber of two neighboring first deforming elements 21*a* is filled and the corresponding other chamber of the two neighboring first deforming elements 21*a* is emptied. When the resting area of the head extends over more than two deforming elements 21, corresponding deformations of more than two deforming elements 21 can be made to achieve a corresponding tilting of the head.

To achieve an active tilting of the head into a longitudinal direction L perpendicular to the cross-direction Q, two or more second deforming elements 21*b* can be provided which abut along the row of first deforming elements 21 extending in cross-direction Q with respect to the longitudinal direction L, and which have substantially the same width as the row of the first deforming elements 21*a*. In the shown embodiment, the second deforming element 21*b* extends along the whole width of the arrangement of the first deforming elements 21*a*.

Variations of the arrangement of deforming elements 21 are possible, however these should be arranged so that the height of the head support 2 in the section in which the deforming elements 21 are arranged or the height difference between the corresponding deforming elements 21 can be set or altered, respectively, by a corresponding actuating of one or more of the deforming elements 21. Particularly, it shall be achieved by the arrangement of the deforming elements 21 that when a head is rested on an active surface of the head support 2 in which the deforming elements 21 are arranged, the corresponding heights of at least the deforming elements 21 below the resting area of the head can be altered so that a tilting of the head at least in the cross-direction Q, preferably also in the longitudinal direction L, can occur.

In above example, the tilting can be carried out in that the deforming elements in the area on which the head rests on the deforming elements 21 can be actuated, so that the height of the head support 2 increases while, in the direction into which the head shall be tilted, the corresponding deforming element 21 is actuated/controlled so that the head support 2 gets a lower height. So, a tilting momentum is applied onto the head, the amount of which substantially depends on the height difference that the head is exposed to by the different settings of the height of the neighboring deforming elements 21.

In the above embodiment, the tilting of the head in the longitudinal direction L by setting the second deforming elements 21*b* can be achieved. Furthermore, for supporting the tilting movement in the longitudinal direction L, the deforming elements 21 arranged in cross-direction Q can be actuated in an opposing manner so that they effectuate a height change, i.e. an increase or a decrease of the height of the head support 2, which is uniform and which acts over the whole width of the arrangement in cross-direction Q with respect to the height change of the second deforming element 21.

The head support 2 is further provided with one or more microphones 24 which allow to record a snoring noise of an individual sleeping on the head support 2. To reliably detect the snoring noise at least two microphones 24 are arranged at the ends of a head support 2 with respect to the cross-section Q. Thereby, the snoring noise of an individual sleeping on one side can be reliably detected.

Apart from microphones 24, the snoring noise can also be detected by a pressure sensor (not shown) arranged within the head support 2 or by an external vibration sensor (not shown).

Furthermore, the head support 2 can be provided with a sensitive laminate, e.g. a laminate with resistive, capacitive or piezoresistive measurement characteristics to detect vibrations caused by snoring noises. Alternatively, a bed frame on which the head support 2 is placed can be provided with a corresponding sensing unit to detect vibrations caused by snoring.

The actuation of the deforming elements 21 is controlled by the external control unit 4. The control unit 4 is in signal connection with an actuating unit 9 in which solenoid valves 92 or other suitable valves for controlling an air intake or air outlet, e.g. spool valves or reed valves, are provided for each of the deforming elements 21*a*, 21*b*. The solenoid valves 92 are electrically controlled by the control unit 4 via the signal connection 11 and are capable of feeding pressurized air supplied via the air conduct 8 to the chambers of the deforming elements 21*a*, 21*b*. In general, the solenoid valve 92 can control the air intake in a direction towards and the air outlet in a direction away from the individual chambers. In other words, the solenoid valve 92 allows each of the chambers to be driven separately so that they can be filled with pressured air or so that the contained air can be released.

The control unit 4 is furthermore signal-connected over an (optional) processing unit 12 with a sensing array 13 of a sensing layer B and the microphones 24 so that the control unit 4 can be supplied with both an electrical microphone signal provided by the microphones 24 and sensor signals provided by the sensing array 13. The processing unit 12 serves to reduce the number of signal lines which are fed to the control unit 4. If at least one of the microphones 24 detects a snoring noise, a corresponding microphone signal is analyzed by the control unit 4 to recognize a snoring or to determine whether or not the detected noise is a snoring noise. For this purpose, a suitable sound recognition algorithm which in principle can comprise a function of a speech recognition algorithm can be implemented in a microcontroller 41 of the control unit 4.

When detecting a snoring noise, the control unit 4 actuates/controls the deforming elements 21 appropriately. For this purpose, the control unit 4 detects the position of the head of the resting surface of the head support 2 by means of the sensing array 13 and determines those deforming elements 21*a*, 21*b* by which a position change of the head can be effectuated. These deforming elements 21*a*, 21*b* are then actuated according to a given algorithm by controlling/driving the solenoid valves 92 in order to achieve a height change of the corresponding deforming elements 21*a*, 21*b* under the head resting thereon. Of course, electromechanical actuators can also be used as deforming elements 21 and can be driven by means of electrical lines by means of the control unit 4.

To perform a specific position change of the head on the head support 2, it is necessary to detect the position of the head on the head support 2 with an accuracy or position resolution, respectively, which is sufficient to identify the deforming elements 21*a*, 21*b* which are needed to change the position of the head. Therefore, as shown in the cross-sectional view of FIG. 2, the sensing layer B arranged in an interior of the head support 2 is provided between the active layer A and the head resting surface K of the head and substantially covers the active layer A. Particularly, the sensing layer B can be directly arranged onto the active layer A.

The sensing layer B can fully or partly cover the active layer A. The sensing layer B can include individual sensing elements to detect an impact of pressure caused by a head resting on an area of the head resting surface K which is associated with the corresponding sensing element or which is arranged directly above the corresponding sensing element, respectively. Particularly, one or more sensing elements can be associated to each of the deforming elements 21, 21a, 21b wherein each sensing element is located preferably at a position of the corresponding deforming element 21, 21a, 21b closest to the head resting surface K.

The sensing layer B should be arranged with respect to the active layer A so that the sensing layer B can be applied with the pressure which is caused by the head of the sleeping individual resting/lying thereon. Particularly, the sensing layer B should be arranged in the interior of the head support so that the active layer A can serve as an abutment for a pressure load.

The active layer A can further include non-actively deformable elements above which the sensing layer B further extends. Particularly, the second deforming element 21b can be replaced by a non-actively deformable support element, particularly a neck support element.

The sensing layer B includes multiple sensing sections in each of which the resting of a head can be detected. The measurement principles in the sensing sections can be based on capacitive or resistive pressure/force measurements as they are known from prior art.

Figure 3:
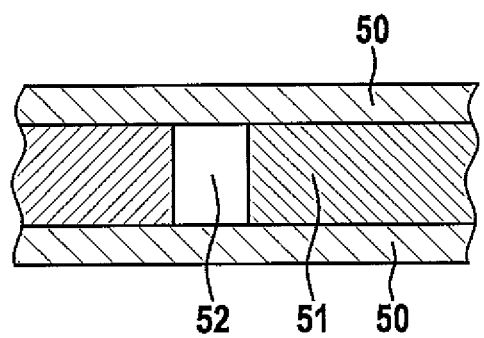
FIG. 3 shows a schematic sectional view of an exemplary sensing layer for use in the head support of FIG. 1.

As shown in FIG. 3, a preferred embodiment of the sensing layer B can include two parallel distanced planar elements 50 for each sensing section, wherein the surfaces of the planar element 50, which are facing each other, are made conductive. For instance, the planar elements 50 can be formed with a flexible laminate or layer, the surfaces of which facing each other, are provided with a metal layer, e.g. a silver layer. Between the planar elements 50, an electrically isolating separation material 51, which is elastically deformable, such as e.g. a foam material or the like, can be arranged. The separation material 51 has one or more openings 52 for each sensing section at which the two conductive surfaces which face each other can electrically contact each other in case a corresponding pressure/force is applied perpendicular to the plane direction. This electrical contacting can be detected separately for each sensing section and can be analyzed in the control unit 4. Thereby, a simple construction of the sensing layer B is possible by which an impact of a force can be detected in a simple manner.

Alternatively an electrical contacting of the two opposing planar elements 50 can be detected, wherein a change of a capacity formed between the planar elements 50 can be detected if the elastically deformable separation material 51 is compressed by applying a pressure/force so that the distance between the planar elements 50 decreases.

As an alternative for the provision of the sensing layer B with pressure sensors, a sensing array with temperature sensors, e.g. a resistive temperature sensor, can be provided in the sensing sections. When the electrical resistance of a sensing element in a sensing section changes so that an increase in temperature can be detected, the presence of a laid-on head can be determined. The detection of the position of the head on the head support 2 by means of the temperature sensors is particularly advantageous as thereby a desirable low-path filtering of the indication of the position of the head is implicitly obtained due to thermal inertia.

In general, the position of the head can be determined by means of a position sensor which allows use of a suitable measurement principle to determine the position of a head resting on the head resting surface K. As a measurement principle, capacitive, resistive and inductive measurement techniques for determining the application of a force/pressure, the application of a temperature and/or a change of the electromagnetic characteristics can be considered for a sensing section of the sensing layer B.

It was found that the position of the head of the head resting surface K cannot be determined with sufficient accuracy or resolution, respectively, if the active layer A is bent with respect to its shape in an unloaded condition or deformed in a different manner due to the own weight of the head, i.e. the arrangement of the individual deforming elements 21a, 21b changes with respect to its direction of alignment in an unloaded condition. In particular, it is often the case that the active layer A is bent due to the load of the head so that it is pressed into the underlay onto which the head support 2 is placed. This results in that the resting area of the head detected by the sensing layer B is too large to be able to accurately determine the actual position of the head. For this reason, it is useful to have a stiffening of the active layer A.

As shown in the cross-sectional view of FIG. 2, this can be achieved by the provision of a backing layer C which opposes the sensing layer B and the head resting surface K with respect to the active layer A. A force/pressure application onto the head resting surface K does not lead to a substantial bending/deformation of the active layer A since it is supported by the backing layer C. The purpose of the backing layer C is to stiffen the active layer A and to support it against a deflection from the direction of alignment in the unloaded condition.

The dimensions of the backing layer C in the longitudinal and cross-directions essentially corresponds to the dimensions of the active layer A. To avoid a direct contact between the individual resting on the head support 2 and the backing layer C, a base layer D can be provided which substantially covers a side of the backing layer C opposing the active layer A and which, together with a comfort layer E which is arranged on a side of the sensing layer B opposing the active layer A, encompass the backing layer C, the active layer A and the sensing layer B.

The base layer D and the comfort layer E are made from a conventional material for pillows, e.g. a cushion material, such as a foam material or the like, to provide softness and comfort as desired.

For assuring a secure support of the backing layer C and the active layer A, the base layer can include elevated edges so that a well/bowl shape is formed. The well/bowl shape supports at least the backing layer C against a sliding into the lateral direction (along the cross-direction Q or the longitudinal direction L, respectively).

The backing layer C is preferably made of a material which has a higher stiffness than the material of the base layer D. For instance, as materials for the backing layer C, a plastic material, a metal and/or a natural fiber material can be considered which have none or only a marginal bending if the head resting surface K is loaded with the weight of a head. In particular, the material should be selected so that a possible bending of the backing layer C does not result in a detection of a resting area of the head which is larger than the actual resting area of the head on the head resting surface K.

To avoid a sliding of the active layer A on the backing layer C, the active layer A is mounted on the backing layer C. For instance, the active layer A can be adhered onto the backing layer C. In an alternative embodiment, the active layer A can be sewed onto the backing layer C. For this purpose, the active layer A can include deforming elements 21a, 21b with fillable chambers, and the backing layer C can be made of a natural fiber material such as jute. The sewing can be carried out so that seams are located between the chambers.

Analogously, the sensing layer B can be connected with the active layer A and the backing layer C by adhering or by sewing to avoid a sliding of the sensing layer B on the active layer A. This is particularly important, since the associating of the sensing sections of the sensing layer B with respect to the deforming elements 21a, 21b under the sensing layer B have to be distinct/defined to allow an identification of the deforming elements 21a, 21b to be actuated.

The invention claimed is:

1. A head support for stopping snoring of a sleeping individual, comprising:
    a head resting surface for the head of a sleeping individual to rest on;
    an active layer with an arrangement of neighboring deforming elements for controlling the height of the head support section by section; and
    a sensing layer which is arranged in an interior of the head support between the head resting surface and the active layer to detect a position of the head resting on the head resting surface, the sensing layer substantially covering the active layer, wherein the sensing layer has individual sensing sections which detect the position of a head on the head support by identifying one or more of the individual sensing sections on which the head of the sleeping individual rests, so that the deforming elements which are needed to change the position of the head are identifiable.

2. The head support according to claim 1, wherein a stiffening element is provided to counteract a deflection of the active layer in the direction of a weight force of the head resting on the head resting surface.

3. The head support according to claim 2, wherein the stiffening element comprises a backing layer which is arranged on the side of the active layer which faces away from the sensing layer.

4. The head support according to claim 3, wherein the active layer is attached to the backing layer by one of adhering or sewing, and/or the active layer is attached to the sensing layer by one of adhering or sewing.

5. The head support according to claim 3, wherein the backing layer is sandwiched between a base layer and the active layer, wherein the base layer has a lower stiffness than the backing layer.

6. The head support according to claim 5, wherein a comfort layer is sandwiched between the head resting surface and the sensing layer, and the base layer and the comfort layer together fully enclose the backing layer, the active layer and the sensing layer.

7. The head support according to claim 1, wherein the deforming elements of the active layer comprise chambers fillable with a medium, wherein the medium is supplied via a conduct by a pump provided external to the head support, and a sound-dampening device is arranged on or in the conduct to dampen vibrations in the medium.

8. The head support according to claim 1, wherein the sensing sections include one or more resistive, capacitive pressure sensors, one or more pressure-sensitive contact elements or one or more temperature sensors, and the sensing sections are arranged so that the position of the head is detectable by identifying one or more of the sensing sections on which the head rests/lies on.

9. A system comprising:
    the head support according to claim 1; and
    a control unit in communication with the sensing layer, the sensing layer supplying the control unit with a signal which identifies one or more of the sensing sections on which pressure is being exerted by the head of the sleeping individual to cause the control unit to actuate one or more of the appropriate deforming elements to change a height of the head resting surface.

10. The system according to claim 9, wherein the control unit detects snoring of an individual resting on the head support and actuates the deforming elements to change the position and/or the orientation of the head when the snoring has been detected.

11. An arrangement for stopping snoring of a sleeping individual, comprising:
    a control unit;
    a head support comprising:
        an upper area defining a resting surface thereon;
        an active layer including a plurality of individual height-adjusting elements arranged along said head support beneath said head resting surface, each said height-adjusting element being actuable by said control unit to cause a change in height of said head resting surface; and
        a sensing layer in communication with said control unit and disposed within an interior of said head support between said head resting surface and said active layer, said sensing layer substantially covering said active layer and having a plurality of individual sensing elements, each said sensing element being disposed to detect pressure exerted by a head of the sleeping individual resting on a portion of said head resting surface corresponding to said sensing element, said sensing layer supplying said control unit with a signal which identifies one or more of said sensing elements on which pressure is being exerted by the head of the sleeping individual, said signal causing said control unit to actuate one or more of said height-adjusting elements disposed substantially beneath said portion of said head resting surface to change a height thereof.

12. The arrangement according to claim 11, wherein said plurality of height-adjusting elements includes a plurality of first height-adjusting elements disposed in side-by-side adjacent relation with one another in a row along said head support beneath said head resting surface, and at least one second height-adjusting element disposed adjacent said first height-adjusting elements and beneath said head resting surface, said first height-adjusting elements when actuated by said control unit actively tilting the head of the sleeping individual in a first direction and said second height-adjusting element when actuated by said control unit actively tilting the head of the sleeping individual in a second direction which is transverse to the first direction.

13. The arrangement according to claim 11, wherein each said sensing element is disposed to detect pressure exerted by a head of the sleeping individual resting on a portion of said head resting surface which is located directly above said sensing element.

14. The arrangement according to claim 11, wherein said active layer and said sensing layer are fully enclosed and contained within said head support beneath said head resting surface.

15. The arrangement according to claim 11, wherein each said height-adjusting element comprises an element which is deformable in shape upon actuation by said control unit to change a height of said head resting surface.

16. The arrangement according to claim 11, further including a backing layer disposed on a side of said active layer which faces away from said sensing layer, said backing layer being of a stiffness sufficient to counteract a deflection of said active layer in a direction away from said head resting surface and corresponding to a direction of a force exerted by the head of the sleeping individual acting on said head resting surface.

17. The arrangement according to claim 16, further including a comfort layer disposed between said head resting surface and said sensing layer and a base layer of a lesser stiffness than said backing layer, said backing layer being disposed between said active layer and said base layer, and said base layer and said comfort layer together fully enclosing said backing layer, said active layer and said sensing layer.

18. A head support for stopping snoring of a sleeping individual, said head support comprising:
   an upper surface defining a head resting surface thereon;
   an active layer including a plurality of individual height-adjusting elements arranged along said head support beneath said head resting surface, each said height-adjusting element being configured to cause a change in height of said head resting surface; and
   a sensing layer disposed within an interior of said head support between said head resting surface and said active layer, said sensing layer substantially covering said active layer and including a plurality of individual sensing elements, each said sensing element detecting pressure exerted by a head of the sleeping individual resting on a portion of said head resting surface corresponding to said sensing element to actuate one or more of said height-adjusting elements disposed substantially beneath said portion of said head resting surface to change a height thereof.

19. A system comprising the head support of claim 18, and a control unit in communication with said sensing layer, said sensing layer supplying said control unit with a signal which identifies one or more of said sensing elements on which pressure is being exerted by the head of the sleeping individual, said signal causing said control unit to actuate one or more of said height-adjusting elements disposed substantially beneath said portion of said head resting surface to change a height thereof.

* * * * *